US008251990B2

(12) United States Patent
Kaouk (10) Patent No.: US 8,251,990 B2
(45) Date of Patent: Aug. 28, 2012

(54) APPARATUS AND METHOD OF PERFORMING RADIOFREQUENCY CAUTERIZATION AND TISSUE REMOVAL

(75) Inventor: Jihad Kaouk, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 897 days.

(21) Appl. No.: 11/726,446

(22) Filed: Mar. 21, 2007

(65) Prior Publication Data
US 2007/0225702 A1   Sep. 27, 2007

Related U.S. Application Data (60) Provisional application No. 60/784,232, filed on Mar. 21, 2006.

(51) Int. Cl.
*A61B 18/14* (2006.01)
(52) U.S. Cl. ........................................... 606/41
(58) Field of Classification Search ............... 606/41–50
See application file for complete search history.

(56) References Cited

U.S. PATENT DOCUMENTS

| 5,354,295 | A  | * | 10/1994 | Guglielmi et al. | 606/32  |
|-----------|----|---|---------|------------------|---------|
| 5,817,092 | A  | * | 10/1998 | Behl             | 606/41  |
| 5,827,276 | A  | * | 10/1998 | LeVeen et al.    | 606/41  |
| 6,179,832 | B1 | * | 1/2001  | Jones et al.     | 606/32  |
| 6,443,970 | B1 | * | 9/2002  | Schulze et al.   | 606/171 |
| 6,638,277 | B2 |   | 10/2003 | Schaefer et al.  |         |
| 6,676,660 | B2 | * | 1/2004  | Wampler et al.   | 606/51  |
| 6,855,140 | B2 |   | 2/2005  | Albrecht et al.  |         |
| 2004/0133196 | A1 |   | 7/2004 | Schaefer et al.  |         |
| 2004/0267256 | A1 |   | 12/2004 | Garabedian et al. |        |
| 2005/0033285 | A1 |   | 2/2005 | Swanson et al.   |         |
| 2005/0251134 | A1 |   | 11/2005 | Woloszko et al.  |         |
| 2006/0025765 | A1 |   | 2/2006 | Landman et al.   |         |

OTHER PUBLICATIONS

Ritz et al., In-Vivo Evaluation of a Novel Biopolar Radiofrequency Device for Interstitial Thermotherapy of Liver Tumors During Normal and Interrupted Hepatic Perfusion, Journal of Surgical Research 133, 176-184 (2006).

* cited by examiner

*Primary Examiner* — Michael Peffley
*Assistant Examiner* — Daniel Fowler
(74) *Attorney, Agent, or Firm* — Tarolli, Sundheim, Covell & Tummino LLP (57) ABSTRACT

An apparatus for cauterizing and severing tissue from a patient's body is provided. The apparatus includes a sheath and a cauterization device. The sheath is adapted for insertion into the body. The sheath has a tubular cross-section and includes longitudinally spaced proximal and distal ends. The cauterization device includes a main body portion and a plurality of electrodes for contacting and cauterizing the tissue. Each electrode has longitudinally spaced proximal and distal ends and extends longitudinally through the sheath. The distal end of each electrode is adapted to selectively protrude from the distal end of the sheath to contact and cauterize the tissue. At least one of the plurality of electrodes includes at least one cutting edge formed adjacent the distal end for severing cauterized tissue from the body upon rotation of the main body portion.

13 Claims, 4 Drawing Sheets

APPARATUS AND METHOD OF PERFORMING RADIOFREQUENCY CAUTERIZATION AND TISSUE REMOVAL

RELATED PATENT APPLICATION

This application claims priority to the filing date of U.S. Provisional Application No. 60/784,232, filed Mar. 21, 2006.

TECHNICAL FIELD

The present invention relates to an apparatus and method for performing radiofrequency ("RF") cauterization and tissue removal and, more particularly, to excision of tumor tissue using RF electrodes equipped with cutting edges.

BACKGROUND OF THE INVENTION

The use of RF energy for achieving hemostasis, or cessation of bleeding, within a patient's body is known in the art. It is known to insert an RF electrode, for example, into the patient's body and then heat the electrode so that a target tissue is cauterized and may then be cut without bleeding. The RF electrode typically comprises an exposed conductive tip portion and an insulated portion covering the remainder of the electrode. Heating of tissue occurs at the exposed conductive tip portion when the RF electrode is connected to an external power source. Consequently, therapeutic changes in the target tissue are created by elevated tissue temperature near the conductive tip portion.

This RF cauterization technique may be used, for example, in treating human renal tumors through destroying and optionally removing the tumor tissue. An RF electrode is placed into contact with the tumor tissue to cauterize the tissue. Because the RF energy does not travel far from the conductive tip portion, the RF electrode must be repeatedly repositioned and reenergized until all of the tumor tissue is cauterized or destroyed. However, the surgeon must take care not to char the tumor tissue or to leave a portion of the tumor accidentally intact/uncauterized, while moving the RF electrode accurately and precisely to minimize damage to healthy tissue.

Once the tumor is completely cauterized throughout, it can be left in place for reabsorption by the body, or the surgeon may cut out and remove the tumor using known minimally invasive surgical tools. In either case, however, the tissue of the tumor is destroyed and cannot be tested or used for other diagnostic or research purposes. Additionally, excision of a cauterized tumor may result in damage to nearby healthy kidney tissue. If such damage results in bleeding, the blood supply to the kidney is normally temporarily clamped off so that the damaged healthy areas can be sutured or otherwise treated to prevent further bleeding; interruption of blood supply to an organ can result in deprivation-related damage, so bloodflow is generally sought to be preserved. Finally, if the tumor is not completely cauterized or destroyed before removal, the severance of the tumor from the organ may result in a release of live tumor tissue into the patient's body, possibly causing future tumor growth within the body and necessitating additional surgical procedures or other treatment.

Treatment of a tumor using RF cauterization may therefore be very time-consuming and complex for the surgeon. The RF cauterization surgeon also ruins an otherwise useful tumor tissue sample and possibly risks damage to healthy organ tissue or spreading of live tumor tissue within the patient's body.

Accordingly, it is desirable to provide a method and apparatus of cauterizing and removing tissue from a patient's body which: avoids time-consuming repositioning of electrodes and repeated application of RF energy, preserves the natural characteristics of the removed tissue, minimizes RF or blood-deprivation damage to healthy tissue, avoids additional suture work by the surgeon, may be used in a timely and efficient manner, and is more economical to manufacture and use.

SUMMARY OF THE INVENTION

In an embodiment of the present invention, an apparatus for cauterizing and severing tissue from a patient's body is described. The apparatus includes a sheath and a cauterization device. The sheath is adapted for insertion into the body. The sheath has a tubular cross-section and includes longitudinally spaced proximal and distal ends. The cauterization device includes a main body portion and a plurality of electrodes for contacting and cauterizing the tissue. Each electrode has longitudinally spaced proximal and distal ends and extends longitudinally through the sheath. The distal end of each electrode is adapted to selectively protrude from the distal end of the sheath to contact and cauterize the tissue. At least one of the plurality of electrodes includes at least one cutting edge formed adjacent the distal end for severing cauterized tissue from the body upon movement of the main body portion.

In an embodiment of the present invention, a method of removing a tumor from a tissue within a patient's body is described. According to the inventive method, a radiofrequency cauterization device having a main body portion and a plurality of electrodes, at least one electrode including a cutting edge, is provided. The electrodes are inserted into the patient's body and positioned in contact with the tissue adjacent to the tumor. Radiofrequency energy is provided to at least one electrode. The tissue adjacent to the tumor is cauterized with the radiofrequency energy to produce cauterized tissue and surrounding tissue which is not cauterized. The main body portion is selectively moved. The plurality of electrodes are selectively moved. The cauterized tissue is severed with the cutting edge of at least one electrode to excise the tumor and at least a portion of the cauterized tissue from the surrounding tissue. The severed cauterized tissue and tumor are extracted from the body.

BRIEF DESCRIPTION OF THE DRAWINGS

For a better understanding of the invention, reference may be made to the accompanying drawings, in which.

DESCRIPTION OF EMBODIMENTS

Figures 1, 2, 3:
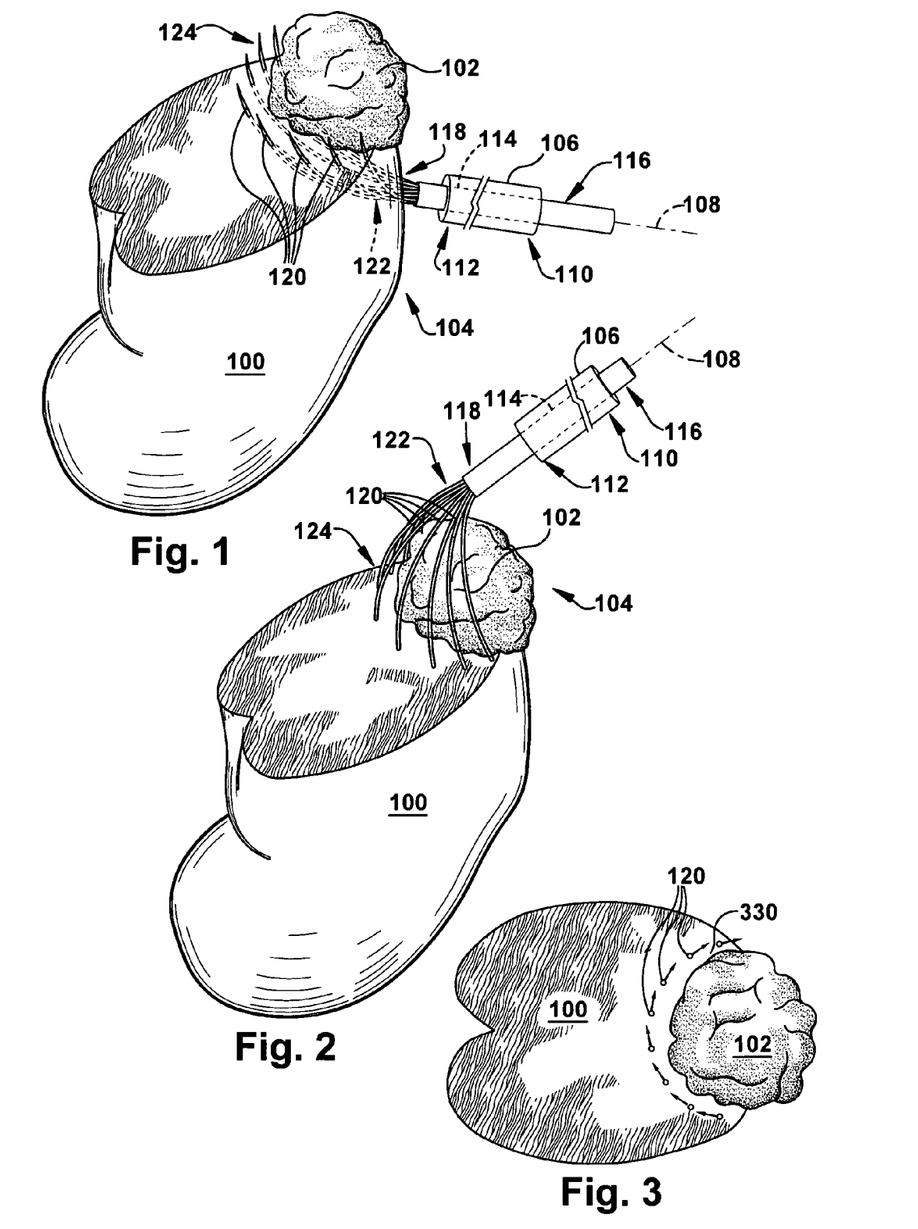
FIG. 1 is a perspective view of a first embodiment of the present invention in a first mode.
FIG. 2 is a perspective view, similar to that of FIG. 1, of the present invention in a second mode.
FIG. 3 is a partial top view of the embodiment of FIG. 1.

In accordance with a first embodiment of the present invention, FIGS. 1-3 each depict a partial view of an organ 100, shown in FIG. 1 as a kidney, with a portion of the organ removed (the cut plane is indicated by shading) to more clearly depict a tumor 102 growing into the organ. A radiofrequency ("RF") cauterization device 104 engages the tumor 102 to cauterize and sever the tumor from the organ 100.

Though the following description uses the terms "organ" and "tumor" to differentiate between the healthy and diseased, or wanted and unwanted, body tissues, respectively, the present invention may be used to cauterize and sever any unwanted tissue from any area of the body. "Organ" and "tumor" are not limiting upon the present invention, but are merely used for ease of description herein.

Likewise, this description refers to engagement, cauterization, and severance of a tumor 102, which can optionally be done via engagement, cauterization, and severance of a border or margin of healthy tissue located adjacent the tumor and which separates the tumor from the rest of the organ 100, as shown by the position of the RF cauterization device 104 in FIGS. 1-3. A partial nephrectomy is an example of such a process. Removing the tumor 102 by cauterizing and severing some amount of bordering healthy tissue generally results in more complete containment and removal of the tumor tissue than would be possible if only the tumor itself were targeted for cauterization and removal. When this bordering technique is used, the tumor 102 itself need not undergo any cauterization or severance, but may instead be removed intact from the organ 100. A surgeon, however, may instead choose to cauterize and sever the tumor 102 directly without cauterizing or severing adjacent healthy tissue, based upon the position of the tumor on the organ 100, the type of tumor, or any other factors. Such a borderless, tumor-only procedure could be accomplished with the RF cauterization device 104 of the present invention similarly to the bordered procedure described herein, and will not be further discussed.

The RF cauterization device 104 according to an embodiment of the present invention includes a sheath 106 adapted for insertion into the patient's body, optionally through a previously inserted trocar or lumen. The sheath 106 is tubular in cross-section, having a hollow interior in a similar structural arrangement to those of known lumens and cannulae, and has a longitudinal axis 108. The sheath 106 has longitudinally spaced proximal and distal ends 110 and 112, respectively, and may have a pointed or sharpened tip (not shown) at the distal end to aid in smoothly inserting the sheath into the body or otherwise to position the sheath into a desired relationship with the targeted tissue. The sheath 106 can have multiple variations in construction, material, and/or geometry. The sheath 106 may be fully insulated, partially insulated, or not insulated at all, depending on construction needs. The diameter and length of the sheath 106 may vary as needed; only a partial length of the sheath is shown in FIGS. 1 and 2, for clarity.

The proximal end 110 of the sheath 106 can have a rigid, semi-rigid, or flexible configuration and may include one or more mechanisms (not shown) for attaching different external devices (e.g., energy sources, visualization tools, etc.). The proximal end 110 may also include at least one locating means (not shown) including, for example, visible markings to indicate how far the sheath 106 has been advanced into the patient's body. The visible markings can also be used to indicate twisting motions of the sheath 106—i.e., to indicate the radial orientation of the guidable distal end 112 relative to the proximal end 110.

The proximal end 110 may also include at least one control element (not shown) to provide control over the operation of the sheath 106. For example, the proximal end 110 may be attached to or shaped into a handle (not shown). The handle may be comprised of metal, plastic, or other compositions. The handle may facilitate gripping of the sheath 106 to improve steering capability so that the sheath can be steered or directed as desired. Other control elements, such as plungers (not shown) or buttons (not shown) that act on mechanical, hydrostatic, electrical, or other types of controls may also or instead be provided to the sheath 106.

The distal end 112 of the sheath 106 has sufficient rigidity to advance within the patient's body and approach the tumor 102 in response to an axial force exerted on the proximal end 110 of the sheath. The distal end 112 of the sheath 106 need not have an identical structure to the rest of the sheath, and may be a floppy helical spring or a more rigid bent structure with some shape memory. The distal end 112 may also or instead be a resilient structure with a permanent curve, depending on the needs of stiffness, floppiness, and curvature to accommodate different structures of the organ 100.

The RF cauterization device 104 further includes a main body portion 114 having longitudinally separated proximal and distal ends 116 and 118, respectively. The main body portion 114 may be a rod or other suitable structure. The distal end 118 of the main body portion 114 includes a plurality of electrodes 120. The electrodes 120 extend longitudinally through the hollow interior of the sheath 106. Each electrode 120 has longitudinally spaced proximal and distal ends 122 and 124, respectively. The distal end 122 of each electrode 120, and optionally the distal end 118 of the main body portion 114, is adapted to selectively protrude from the distal end 112 of the sheath 106 for positioning at least a portion of the electrode in contact with the tissue to be cauterized and severed. At least one of the electrodes 120 is capable of delivering RF energy to the selected area of tissue. The electrodes 120 may be of any suitable material or construction. For example, the electrodes 120 may comprise a metal tube or blade, a wire structure, or the like, and may be comprised of a conductive material such as stainless steel, Nitinol, Nitinol-based alloys, copper, cobalt alloys, titanium, or the like. The electrodes 120 may be of differing shapes, functions, and/or compositions in a single RF cauterization device 104, and may readily be chosen for a particular application by one of ordinary skill in the art.

Figures 4, 5B:
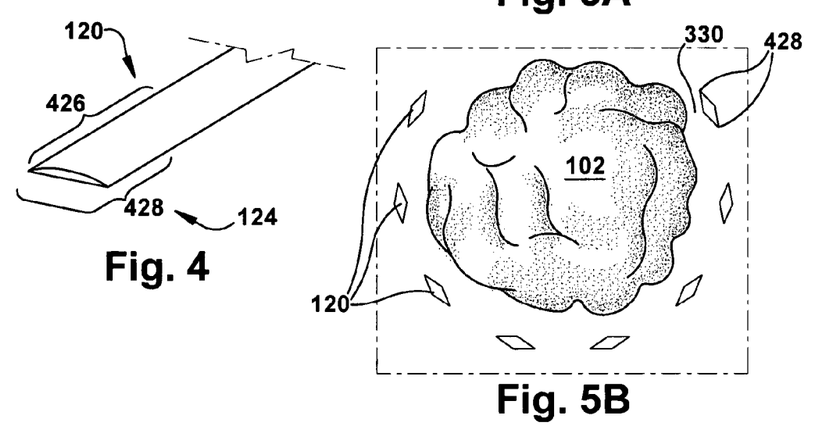
FIG. 4 is a partial detail view of the first embodiment of the present invention.
FIGS. 5A-5C are partial cross-sectional views, similar to that of FIG. 3, of alternate configurations of the present invention.

The distal end 124 of an electrode 120 according to an embodiment of the present invention is shown in partial close-up in FIG. 4. An energy transmitting region 426 of the electrode 120 may comprise the entire length of the distal end 124 of the electrode or, alternatively, may be restricted to a portion that is less than the entire length of the distal end, as shown in FIG. 4. Where the energy transmitting region 426 includes a portion less than the entire length of the distal end 124, the energy transmitting region may include at least one band (not shown) or link (not shown) capable of delivering the energy to the energy transmitting region without undesirably energizing the rest of the distal end.

At least one electrode 120 may also or instead include at least one resistive heating element (not shown) so, for example, the energy transmitting region 426 heats up by resistive heating of the resistive heating element. Where the energy transmitting region 426 includes a resistive heating element, there may be a resistive wire (not shown) such as a nichrome wire or other type of resistive heating element capable of delivering current to the resistive element so that heating occurs within the resistive heating element.

An energy source (not shown) provides energy to the plurality of electrodes 120. As described above, the energy source may be operatively connected to the proximal end 110 of the sheath 106. The energy source may be a source of high frequency current, voltage, or power; an ultrasonic source; a source of laser or electromagnetic energy; a resistive power heating source; or the like.

As one specific example, the energy source may be an RF generator with a frequency output range between several kilohertz and several hundred megahertz, and a power output range from several watts to several hundred watts, depending on clinical need. The energy source may have control devices (not shown) to increase or modulate power output as well as readout and display devices (not shown) to monitor energy parameters such as voltage, current, power, frequency, impedance, and so forth.

At least one electrode 120 includes at least one cutting edge 428 formed adjacent to or on the distal end 124 of the electrode. The cutting edge 428 may have any desired structure or orientation on the electrode 120 that is operative to selectively mechanically sever the tumor 102 from the organ 100. For example, the cutting edge 428 could be a sharpened, smooth surface similar to that of a scalpel blade. An electrode 120 equipped with a cutting edge 428 may also include an energy transmitting region 426. The cutting edge 428 and energy transmitting region 426 of each electrode 120 need not be coincident in position, extent, or configuration with respect to the electrode. The energy transmitting region 426 may be adapted to sever tissue using RF energy, in addition to the mechanical severance provided by the cutting edge.

Figure 5A:
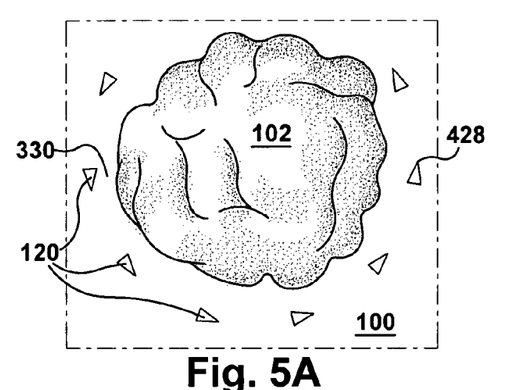
Figure 5C:
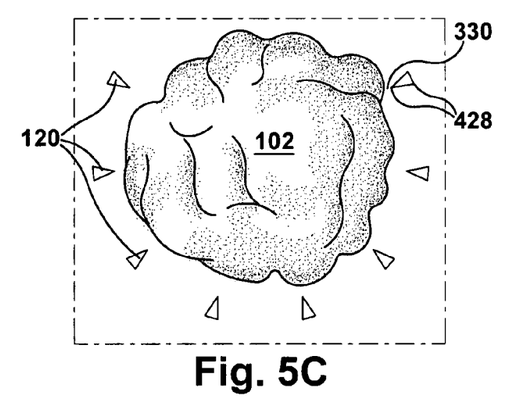

FIGS. 5A-5C depict examples of suitable arrangements of the location and orientation of the cutting edges 428 with respect to the plurality of electrodes 120. The structures of FIGS. 5A-5C are not intended to limit the present invention in any way, however, and one of ordinary skill in the art can readily design electrodes 120 having cutting edges 428 and/or energy transmitting regions 426 suited for any application of the present invention.

The sheath 106 may include at least one radiographically opaque marking (not shown). The radiographically opaque marking may be located at the distal end 112 of the sheath 106. Alternatively or additionally, one or more radiographically opaque markings may be located at the distal ends 124 of the electrodes 120. The radiographically opaque marking may be any one or combination of materials or devices with significant radiopacity. Examples of such radiographically opaque markings include, but are not limited to, a steel mandrel sufficiently thick to be visible on fluoroscopy, a tantalum\polyurethane tip, a gold-plated tip, bands of platinum, stainless steel or gold, soldered spots of gold, and polymeric materials with a radiographically opaque filter such as barium sulfate. Direct observation by radiographic imaging may facilitate advancement and positioning of the sheath 106 and/or electrodes 120. Such radiographically opaque markings are especially desirable when a portion of the electrodes 120 or sheath 106 is not clearly visible through radiographic imaging.

The RF cauterization device 104 is used to remove a tumor 102 or other unwanted tissue from an organ 100 or other tissue of a patient's body. The tumor 102 is first identified using a known imaging method. Examples of known imaging methods include magnetic resonance imaging (MRI), X-ray, computed tomography (CT), ultrasound, and positron emission tomography (PET).

After the tumor 102 has been identified, an appropriately-sized sheath 106 is selected. The size, geometry, and/or configuration of any portion of the RF cauterization device 104 may differ depending on the position, size, and/or composition of the tumor 102 to be treated. The sheath 106 is then inserted through the patient's skin and directed toward the tumor 102, possibly penetrating at least a portion of the organ 100 on which the tumor is located. Prior to insertion of the sheath 106 into the patient's body, the sheath 106 may be fitted with an internal removable obturator (not shown) or trocar (not shown) to prevent clogging during initial insertion.

Once inserted, the positioning of the sheath 106 can be monitored, controlled, and/or quality assured by imaging systems of various kinds. For example, X-ray machines, fluoroscopic machines, ultrasound, CT, MRI, PET, and other imaging devices may be used. Use of imaging systems to percutaneously place surgical sheaths or other similar devices into the body is known in the art.

After the sheath 106 has been inserted into the body, the distal end 112 of the sheath 106 is positioned within the body as desired. For example, when the tumor 102 is attached to the kidney 100, the sheath 106 may be positioned as shown in FIGS. 1 and 2. The distal ends 124 of the plurality of electrodes 120 are then extended beyond the distal end 112 of the sheath 112 and into contact with a border 330 of organ tissue adjacent the tumor 102, shown best in FIG. 3. Optionally, and as shown best by the dashed lines in FIG. 1, the electrodes 120 may be inserted into or through the organ 100 to the desired positioning in the border 330 adjacent the tumor 102. The electrodes 120 should be positioned to cauterize and sever the border 330 of healthy tissue on the organ 100 adjacent the tumor 102, to allow the tumor to remain largely intact for at least the aforementioned reasons.

Once the distal ends 124 of the electrodes 120 are properly positioned in contact with the border 330, the proximal end 110 of the sheath 106 may be connected to an energy source. If the energy source is a high frequency, RF, microwave, DC current, AC current, laser power, or ultrasonic power source, this connection will enable thermal energy to emanate from the energy transmitting region 426 to the border 330. The thermal energy then cauterizes the portions of the border 330 nearest to the electrodes 120. The tissue of the border 330 is cauterized to allow for largely bloodless severance later. The electrodes 120 may be repositioned as needed to cauterize the border 330, to ensure a desired separation of tumor tissue from the healthy tissue of the organ 100 by a cauterized border.

Appropriate amounts of power, current, thermal heat, or light energy are produced by the energy source and delivered to the tumor 102 for a certain amount of time as determined to be appropriate for clinical needs. When the desired amount and time duration of energy delivery for cauterization has been accomplished, the energy transmission to the border 330 is discontinued and the tumor 102 is ready to be severed from the organ 100. Alternately, the electrodes 120 could cauterize tissue as cutting occurs, for desired hemostasizing properties; in such case, activation of the energy transmitting regions 426 of the electrodes is continued while the cutting edges 428 sever the tissue as desired.

To sever the tumor 102 from the organ 100, one or more of the plurality of electrodes 120 is selectively moved so that at least one cutting edge 428 engages the border 330 at the desired point of severance. The cutting edge 428 should be sharp and controllable enough to cut through the cauterized tissue of the border 330 with minimal or no damage to the non-cauterized healthy tissue of the organ 100 adjacent the severance point.

Once the tumor 102 has been severed by separation of the cauterized border 330 from the organ 100, the electrodes 120 may be withdrawn back into the sheath 106 for removal from the patient's body. The severed tumor 102 is normally removed for later use or to avoid future damage to the patient. Removal of unwanted material from a patient's body is known in the art and can be accomplished in several ways, any of which may be employed to extract the severed tumor 102 from the body. For example, the surgeon could simply remove the severed tumor 102 directly from an aperture in the body during an open or laparoscopic surgery. Alternately, a remote forceps (not shown) could grasp the tumor 102 upon severance and retract through a lumen with the tumor 102 contained when minimally invasive surgical techniques are used. In addition to or instead of the forceps, the severed tumor 102 could be enclosed within a bag or other container for removal, possibly to avoid contamination of adjacent tissues or disintegration of the tumor 102. In any of these cases, any of the plurality of electrodes 120 could assist in maneuvering the severed tumor 102 for removal from the body through the sheath 106 or a separately provided lumen, though preferably a portion of the electrodes without a cutting edge 428 actually contacts the tumor, to avoid unwanted dissection of the tumor.

FIGS. 6A-8B depict an RF cauterization device 104' in accordance with a second embodiment of the present invention. Features of FIGS. 6A-8B that are the same as or similar to those described with regard to FIGS. 1-5B are given the same reference numbers with the addition of a single prime. Description of common elements and operation similar to those in the first embodiment will not be repeated with respect to the second embodiment.

Figure 6A:
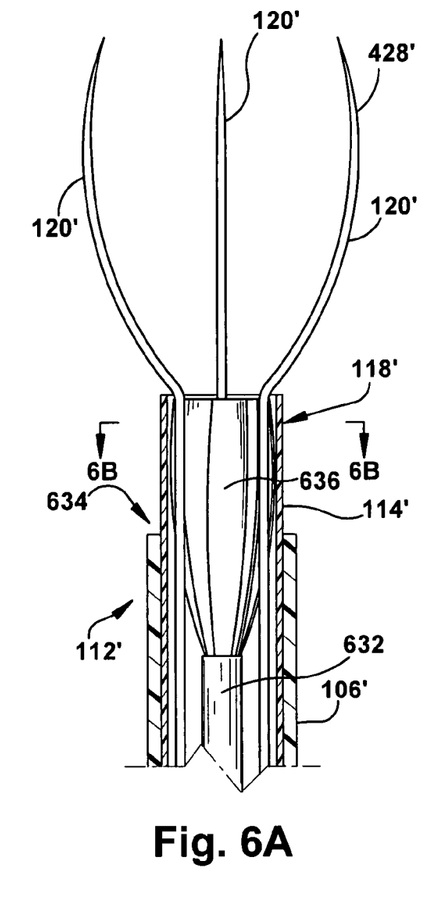
FIG. 6A is a partial cross-section of a second embodiment of the present invention in a first mode.
Figure 6B:
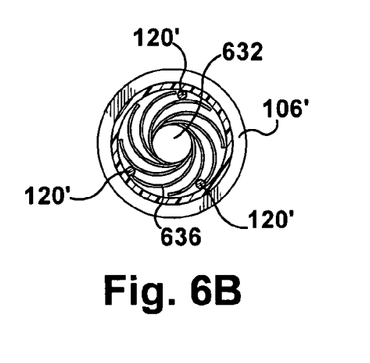
FIG. 6B is a partial cross-sectional view taken along line 6B-6B of FIG. 6A.
Figure 7A:
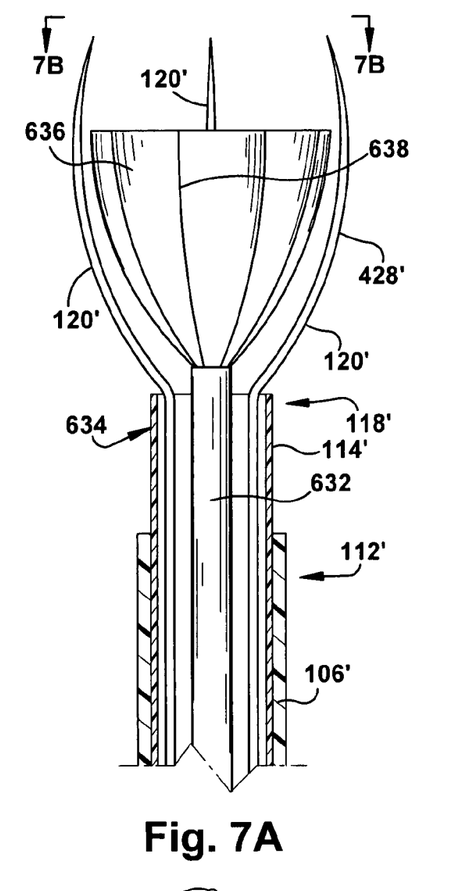
FIG. 7A is a partial cross-section similar to that of FIG. 6A, of the present invention in a second mode.
Figure 7B:
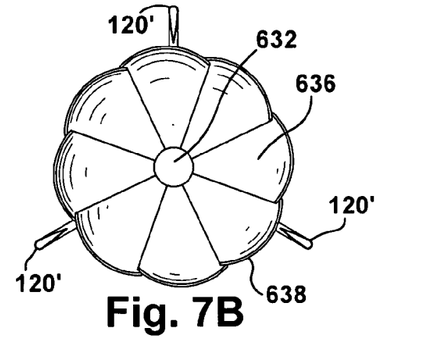
FIG. 7B is a partial cross-sectional view taken along line 7B-7B of FIG. 7A.

FIG. 6B depicts a sheath 106' with a main body portion 114' extending from the distal end 112' of the sheath. A plurality of electrodes 120' extend from a distal end 118' of the main body portion 114'. An inner sheath 632 extends longitudinally through a hollow center of the main body portion 114'. The inner sheath 632 has longitudinally separated distal 634 and proximal (not shown) ends and is adapted for longitudinal motion relative to the main body portion 114'. A plurality of deployable petals 636 extend from the distal end 634 of the inner sheath 632. The petals 636 may be selectively moved between a radially collapsed first condition and a radially expanded second condition.

The petals 636 should be at least partially made of a flexible material such as a polymer, wire mesh, thin metal plate, or the like. The petals 636 may have any suitable size, configuration, shape, or structure to perform the below-described function, and may be readily designed for a particular application of the present invention by one of ordinary skill in the art. For example, the petals 636 could be separately provided and positioned in the nesting or fanning arrangement shown, could be separately provided and held in lateral contact by a hoop (not shown) at any location thereupon, could be integrally formed as a tulip-shaped cup with or without an encircling hoop (not shown), or could have any suitable arrangement or configuration. The plurality of the petals 636 may be physically linked for near-simultaneous movement, or could move independently of each other. The petals 636 could be flexible enough to collapse, or could hold their shape and nest as shown in FIG. 6B. At least two of the plurality of petals 636 may mutually engage to prevent lateral separation or discontinuity between those petals in the second condition.

At least one petal 636 may include a cutting edge 638, similar to the cutting edge 428' of an electrode 120'. The cutting edge 638 may have any desired structure or orientation on the petal 636 that is operative to selectively mechanically sever the tumor 102 from the organ 100. For example, the cutting edge 638 could be a sharpened, smooth surface similar to that of a scalpel blade. A petal 636 may also or instead include an energy transmitting region (not shown), at the cutting edge 638 or any other surface of the petal. A petal 636 including a cutting edge 638 and/or an energy transmitting region could be considered to be an electrode.

Figure 8A:
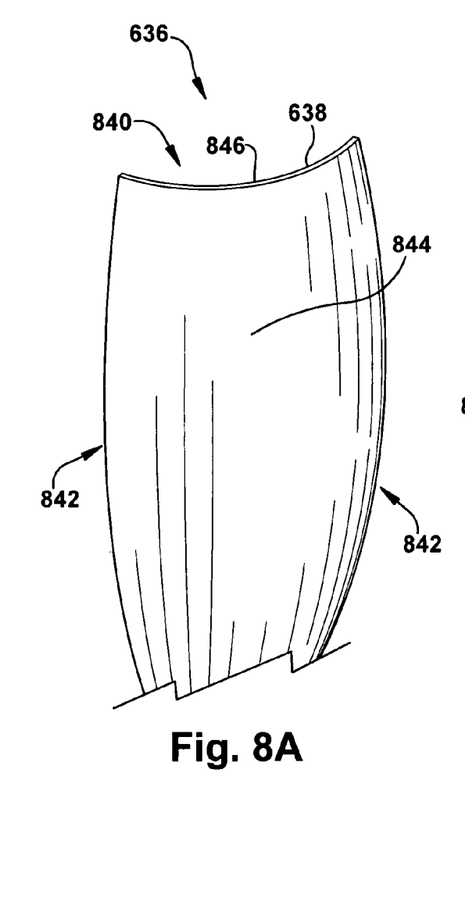
FIG. 8A is a partial detail view of the second embodiment of the present invention in a first configuration.

FIG. 8A partially depicts a petal 636 in the first configuration of FIGS. 6A-7B. A distal petal end 840 at least partially defines a cutting edge 638 as previously described. A pair of petal sides 842 extend between the distal petal end 840 and the inner sheath 632 (omitted from this view for clarity). The petal sides 842 terminate at an end of the petal 636 opposite the distal petal end 840 in an arrangement (not shown) suitable for controlling and retaining the petal 636 as desired, and may include means (not shown) for connecting the petal 636 to the inner sheath 632 or any other portion of the RF cauterization device 104'. A petal surface 844 extends between the distal petal end 840 and the petal sides 842.

The petal 636 could include an energy transmitting region 846 operating similarly to the energy transmitting region 426' of the electrode 120'. As shown in FIG. 8A, the energy transmitting region 846 of the petal 636 is depicted as coincident (at the distal petal end 840) with the cutting edge 638. The energy transmitting region 846 and cutting edge of the petal 638 could be located anywhere on the petal 636 (including the petal surface 844) and could have any mutual relationship or be completely independent of each other.

One or more of the petal sides 842 could include a linking feature (not shown) operative to connect the petal side 842 to a petal side of an adjacent petal (not shown). Optionally, the linking feature allows lateral motion between the two petals to facilitate movement between the first and second conditions.

Figure 8B:
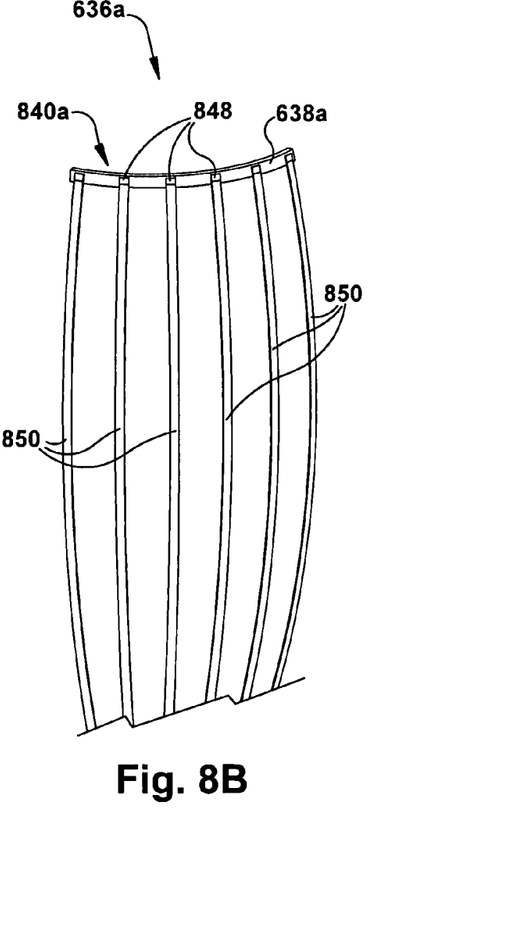
FIG. 8B is a partial detail view of the second embodiment of the present invention in a second configuration.

FIG. 8B partially depicts a petal 636a in a second configuration. Features of FIG. 8B that are the same as or similar to those described with regard to FIG. 8A are given the same reference numbers with the addition of the suffix "a". Description of common elements and operation similar to those in the first configuration of FIG. 8A will not be repeated with respect to the second configuration of FIG. 8B.

In FIG. 8A, the distal petal end 840a is depicted as being a strip of material, at least semi-rigid, containing a plurality of attachment points 848. At least one attachment point 848 is associated with a conduit 850, with each conduit being attached to the distal petal end 840a at an attachment point 848. The attachment point 848 could engage the conduit 850 for affixation to the distal petal end 840a and/or could act as a nozzle or other directional structure for energy carried by the conduit, as set forth below. The conduits 850 may extend between the distal petal end 840a and the inner sheath 632 (omitted from this view for clarity). A cutting edge 638a and/or an energy transmitting region (not shown) may be provided at the distal petal end 840a or at any other location on the petal 636a, as previously described or in any other fashion. The petal 636a of the second configuration could be one of a plurality of petals, similarly to the arrangement of the first configuration shown in FIGS. 6A-7B. Alternatively, the distal petal end 840a could form at least a portion of a circle or hoop shape, causing the petal 636a to take on a cup-shaped or tulip-shaped configuration instead of the depicted flat "leaf" structure.

The conduits 850 may be made of any suitable material and in any desired shape and size, may be flexible or rigid, may be solid or hollow, and may be provided and/or controlled in any suitable manner. The conduits 850 may be of differing shapes, functions, and/or compositions in a single RF cauterization device 104, and may readily be chosen for a particular application by one of ordinary skill in the art. One or more of the conduits 850 of the second configuration of the petal 636a may include a cutting edge (not shown) or an energy transmitting region (not shown). The conduits 850 may be linked at the distal petal end 840a and/or at any location(s) along the length of the conduits 850. The conduits 850 may move separately or together. As with the first configuration of the petals 636, the second configuration 636a could have any suitable structure and could be connected together as desired.

The conduits 850 may be operative to channel energy from the inner sheath 632 or another structure of the RF cauterization device 104 to the distal petal end 840a, to provide or enhance operative functions of a cutting edge and/or an energy transmitting region. For example, the conduits 850 could be optical fibers operative to transmit laser light from a remotely located laser source into the tissue adjacent the distal petal end 840a. The laser could be erbium:yttrium aluminum garnet (Er:YAG); holium:yttrium aluminum garnet (Ho:YAG); neodymium:yttrium aluminum garnet (Nd:YAG); alexandrite, ruby, and potassium titanyl phosphate (KTP); carbon dioxide (CO2); argon; copper vapor; excimer lasers, or any other suitable type.

The conduits 850 could also or instead provide ultrasonic energy, hydrojet/hydraulic energy, electricity, mechanical energy, another type of energy, or any combination thereof to the distal petal end 240a or any other portion of one or more petals 636a. In such manner, the petals 636a can provide severing and/or cauterizing functions to the RF cauterization device 104', alone or in combination with one or more electrodes 120'.

Depending upon the type of energy and the desired application location, the energy could pass through the conduits 850 for open or controlled release from the petal 636a through the attachment points 848. It is contemplated that the structure of the petal 636a could be used to release the energy at a desired location. For example, the conduits 850 could release energy at a location other than through the attachment points 848, such as via a mechanical cutting edge and/or an energy transmitting region along the length of the conduits 850 themselves. As another example, the conduits 850 could form at least a portion of a mesh petal surface (not shown) and release electricity from various locations on the mesh.

Regardless of the configuration of the petals 636, 636a (hereafter referenced as "636"), the RF cauterization device 104' may include means (not shown) for moving the petals 636 between the first and second conditions. For instance, the petals 636 may be moved between the first and second conditions by a spring-loaded device. The petals 636 may also or instead be made of spring steel or a memory-alloy material which naturally moves between the first and second conditions responsive to extension of the inner sheath 632 from the distal end 118' of the main body portion 114', possibly with the assistance of a spreader member (not shown). A movement assistance means (not shown) may have a rigid structure attached to the distal petal end 840 or another portion of the petal 636, and may be adapted to push or pull the petals, singly or together, in a desired direction.

The second embodiment of the present invention is operative to cauterize and sever a tumor (not shown) or other unwanted tissue from an organ (not shown) or other wanted tissue. Operation of the second embodiment's RF cauterization device 104' is similar to that of the first embodiment, with the addition of the petals 636. The petals 636 may be deployed at any suitable point in the operation of the RF cauterization device 104' and may be retracted/re-furled and redeployed as needed. The petals 636 are optionally used to help sever the tumor and/or help contain the tumor and attached cauterized border (not shown) for removal.

As shown in FIGS. 6A-6B, the petals 636 are initially furled within the main body portion 114' in the first condition. As the inner sheath 632 extends longitudinally from the main body portion 114', the petals 636 splay out into the tulip-shaped configuration shown in FIGS. 7A-7B. At least one of the petals 636 should be designed to contact the electrodes 120' for at least a portion of the unfurling/splaying procedure, particularly when the electrodes are used to provide desired guidance and/or containment properties to the expanding petals. However, the contacting relationship is omitted in FIGS. 7A-7B for clarity.

There need not be any specific positional or functional relationship or correlation between the electrodes 120' and the petals 636. The electrodes 120' may act to radially contain the petals 636 in the second condition, or optionally the petals 636 apply radial pressure to radially expand the electrodes 120'. Alternately, neither the electrodes 120' nor the petals 636 have any positioning effect on each other. The electrodes 120' may be, but need not be, attached to at least a portion of a petal 636. In any case, some mutual radial pressure (not shown) may be desirable to maintain contact between the petals 636 and electrodes 120'. This contact, when present, acts to minimize the number of cutting planes along which tissue is separated in the second embodiment of the present invention.

With the petals 636 in the second condition and contacting the electrodes 120', at least one of the cutting edges of the electrodes and petals 428' and 638, respectively, is operative to cut through the cauterized border and sever the tumor from the organ. The severed tumor is then completely separated from the healthy tissue of the organ, yet is cupped, or at least partially contained, within the petals 636.

The severed tumor may be removed from the patient's body as discussed above with respect to the first embodiment—namely, engaged with forceps or enclosed within a bag or other container and removed from the body in an open, laparoscopic, or minimally invasive surgical procedure through the sheath 106 or a separately provided lumen. The petals 636 may be employed to help maneuver the severed tumor and attached cauterized tissue to a desired positioning with respect to the forceps and/or bag for removal. Alternately, the petals 636 may be collapsed to the first, undeployed condition for removal from the patient's body through the main body portion 114' with the severed tumor retained therein.

The movement of the electrodes 120 in any embodiment of the present invention may be accomplished with any suitable mechanism or action, and in any desired combination or order. For instance and as shown by the arrows in FIG. 3, the electrodes 120 could be rotated as a group by rotating the proximal end 116 of the main body portion 114 about the longitudinal axis 108 or a parallel axis, maintaining their relative spacing, to "core out" the cauterized border 330 and attached tumor 102, with each cutting edge 428 traversing a portion of the total severance distance through the border 330. The distal ends 124 of the electrodes 120 could also or instead move longitudinally with respect to the sheath 106 in a "scooping" motion to cut through the cauterized border 330. It is also contemplated that at least one electrode 120 could maintain position to hold the cauterized border 330 in place, while at least one non-stationary electrode traverses the distance between adjacent stationary electrodes to sever the cauterized border 330. Additionally, some of the electrodes 120 could work in concert with other electrodes to cut tissue therebetween in a scissors-like movement, or a similar movement could cut or shear, with relative motion, tissue caught between at least one electrode and a sheath 102. These electrode 120 motions are only given by way of example of any number of suitable selective movements of the electrodes, and do not limit the present invention or any embodiment thereof.

While aspects of the present invention have been particularly shown and described with reference to the preferred embodiment above, it will be understood by those of ordinary skill in the art that various additional embodiments may be contemplated without departing from the spirit and scope of the present invention. For example, the plurality of electrodes 120 may each have one or both of an energy transmitting region and a cutting edge 428. The electrodes 120 could be moved as a group or singly, either to cauterize or sever the tumor 102. A device adjacent the electrodes 120 could capture the severed tumor 102 for withdrawal through the sheath 106. The electrodes 120 could cut tissue which has not been cauterized, or cauterize tissue without cutting except as needed to place and withdraw the electrodes 120. The petals 636 could be adapted to completely enclose the severed tumor. The petal surfaces 844 could be solid or semipermeable, and, as with all other structures of the RF cauterization device, could be made of any suitable materials. A device or method incorporating any of these features should be understood to fall under the scope of the present invention as determined based upon the claims below and any equivalents thereof.

The method and apparatus of certain embodiments of the present invention, when compared with other apparatus and methods, may have the advantages of: avoiding time-consuming repositioning of electrodes and repeated application of RF energy, preserving the natural characteristics of the removed tissue, minimizing RF or blood-deprivation damage to healthy tissue, avoiding additional suture work by the surgeon, being usable in a timely and efficient manner, and being more economical to manufacture and use. Such advantages are particularly worthy of incorporating into the design, manufacture, and operation of RF cauterization devices. In addition, the present invention may provide other advantages which have not yet been discovered.

Other aspects, objects, and advantages of the present invention can be obtained from a study of the drawings, the disclosure, and the appended claims.

Having described the invention, the following is claimed:

1. An apparatus for cauterizing and severing tissue from a patient's body, the apparatus comprising:

a sheath adapted for insertion into the body, the sheath having a tubular cross-section and including longitudinally spaced proximal and distal ends; and a cauterization device including a main body portion and a plurality of electrodes for contacting and cauterizing the tissue, each electrode having longitudinally spaced proximal and distal ends and extending longitudinally through the sheath, the distal end of each electrode adapted to selectively protrude from the distal end of the sheath to contact and cauterize the tissue;

at least one of the plurality of electrodes including at least one sharpened cutting edge formed adjacent the distal end for mechanically severing cauterized tissue from the body upon movement of the main body portion; and wherein at least one of the electrodes has an elongate electrode body, with at least one longitudinally extending electrode edge terminating at a laterally extending distal end of the electrode, and at least one longitudinally extending electrode edge is sharpened along a portion of the length thereof.

2. The apparatus of claim 1, wherein the tissue is at least one of tumor tissue and healthy tissue located adjacent tumor tissue.

3. The apparatus of claim 1, wherein the distal end of the sheath includes means for aiding in positioning the sheath into a desired relationship with the tissue.

4. The apparatus of claim 1, wherein the distal end of at least one electrode is operative to selectively deliver radiofrequency energy to the tissue.

5. The apparatus of claim 4, wherein at least a portion of the distal end of the at least one electrode is an energy transmitting region.

6. The apparatus of claim 5, wherein at least a portion of the energy transmitting region is coincident with the at least one cutting edge.

7. The apparatus of claim 1, wherein the apparatus includes means for removing severed tissue from the patient's body.

8. The apparatus of claim 1, including an inner sheath disposed within the main body portion, the inner sheath having longitudinally spaced proximal and distal ends, and including a plurality of deployable petals selectively extending from the distal end of the inner sheath.

9. The apparatus of claim 8, wherein at least one of the plurality of deployable petals is adapted to assist with at least one of contacting and cauterizing the tissue, severing the cauterized tissue, and containing severed tissue for removal from the patient's body.

10. The apparatus of claim 1, wherein the cauterized tissue is severed through cooperative action of at least one stationary electrode and at least one non-stationary electrode.

11. The apparatus of claim 1, including at least three electrodes.

12. The apparatus of claim 1, wherein a distal end of the main body portion selectively protracts from the distal end of the sheath.

13. The apparatus of claim 1, wherein a distal end of the main body portion includes the plurality of electrodes.

* * * * *